United States Patent [19]

Lewis et al.

[11] Patent Number: 4,764,346
[45] Date of Patent: Aug. 16, 1988

[54] DISPOSABLE REBREATHING CANISTER

[75] Inventors: Ralph H. Lewis, Lakeport; Barnum B. Lambert, San Jose, both of Calif.

[73] Assignee: Pioneer Medical Systems, Inc., San Francisco, Calif.

[21] Appl. No.: 939,743

[22] Filed: Dec. 9, 1986

[51] Int. Cl.$^4$ ............................................. B01D 53/04
[52] U.S. Cl. ..................................... 422/120; 55/387; 55/DIG. 33; 55/DIG. 35; 128/205.12; 128/204.28; 128/205.17; 422/122
[58] Field of Search ................................ 422/120, 122; 128/205.12, 205.15, 202.26, 205.13, 205.27, 205.28, 203.28, 204.28, 205.14, 205.17; 55/DIG. 33, 35, 387

[56] References Cited

U.S. PATENT DOCUMENTS

| | | | |
|---|---|---|---|
| 4,014,326 | 3/1977 | Müller | 128/205.15 |
| 4,459,981 | 7/1984 | Mascher et al. | 128/205.12 |
| 4,502,876 | 3/1985 | Behnke, Jr. et al. | 55/387 |
| 4,567,889 | 2/1986 | Lehmann | 128/205.12 |

Primary Examiner—Michael S. Marcus
Attorney, Agent, or Firm—Ernest M. Anderson

[57] ABSTRACT

A disposable rebreathing canister is disclosed for administering oxygen and anesthesia to patients. The canister essentially comprises a housing for a scrubber, including a manifold plate and a rigid container, and a flexible liner disposed within the rigid container. The liner forms an imperforate barrier between the interior of the rigid container and the manifold plate. A scrubber disposed between the manifold plate and liner chemically reacts with gases conducted to it through one of a pair of coaxial passages formed in the manifold plate. Reacted gases are then moved through a tortuous passage either back to the other one of the coaxial passages or removed through an exhaust port.

The interior of the rigid container connects with a source of pressure that allows the flexible liner to be collapsed, thus forcing treated gases, fresh oxygen and anesthesia into the lungs of the patient.

7 Claims, 2 Drawing Sheets

DISPOSABLE REBREATHING CANISTER

BACKGROUND OF THE INVENTION

This invention relates generally to rebreathing apparatus and more particular to scrubber systems used in conjunction with apparatus to administer oxygen and anesthesia to a patient. In general, rebreathing apparatus commonly used in the prior art is so structured that it is difficult or impossible to maintain sanitized for use with different patients; and in most instances the same $CO_2$ scrubber element is used for more than one patient. At one time it was believed that the soda-lime powder in the element would provide adequate removal of bacteria. However, such is not the case. As shown by many studies, the scrubbers used with anesthetizing apparatus are often found to be the disseminating agent of bacteria. Studies have also shown that numerous pathogenic organisms are found in reservoir bags or bellows which are commonly used with such apparatus.

SUMMARY OF THE INVENTION

This invention provides a disposable rebreathing canister for administering oxygen and anesthesia to a patient. The canister may be readily used and connected to a standard rebreathing apparatus comprising a source of oxygen and anesthsia, reusable anesthesia hoses and a bellows that may be operated to aid in a rebreathing cycle. The canister is so constructed that rebreathing gases are isolated, thus avoiding contamination of major components of the rebreathing apparatus.

The canister of this invention more specially comprises a scrubber housing, including a manifold plate, and a rigid container. The manifold plate is formed with an intake port, an exhaust port, and a pair of coaxial passages. A flexible container is disposed within the rigid container to form an imperforate barrier between the interior space of the rigid container and the intake port, exhaust port, and coaxial passages of the manifold plate. A soda-lime $CO_2$ scrubber is disposed within the flexible container and means is provided connecting one side of the scrubber to the inner one of the coaxial passages and the other side to both the outer one of the coaxial passages and the intake and exhaust ports of the manifold. A bellows is provided for applying pressure between the inner wall of the rigid container and the imperforate flexible liner. This provides a capability for forced rebreathing without contaminating the bellows itself.

A principal object of the present invention is to provide a disposable rebreathing canister for administering oxygen and anesthesia to a patient and which is compatible with existing forms of apparatus.

Another object is to provide a rebreathing canister that may be economically manufactured such that it is disposable after use with a single patient.

A further object of the invention is to provide a disposable rebreathing canister of the kind described which possesses a very low back pressure, and yet is compact in construction.

Other objects of this invention will become apparent in view of the following detailed description.

In the drawings forming a part of this application and in which like parts are identified by like reference numerals throughout the same, FIG. 1 is a perspective view of a preferred embodiment of the invention in a disposable rebreathing canister for administering oxygen and anesthesia;

DETAILED DESCRIPTION OF THE PREFERRED EMBODIMENT

Figure 1:
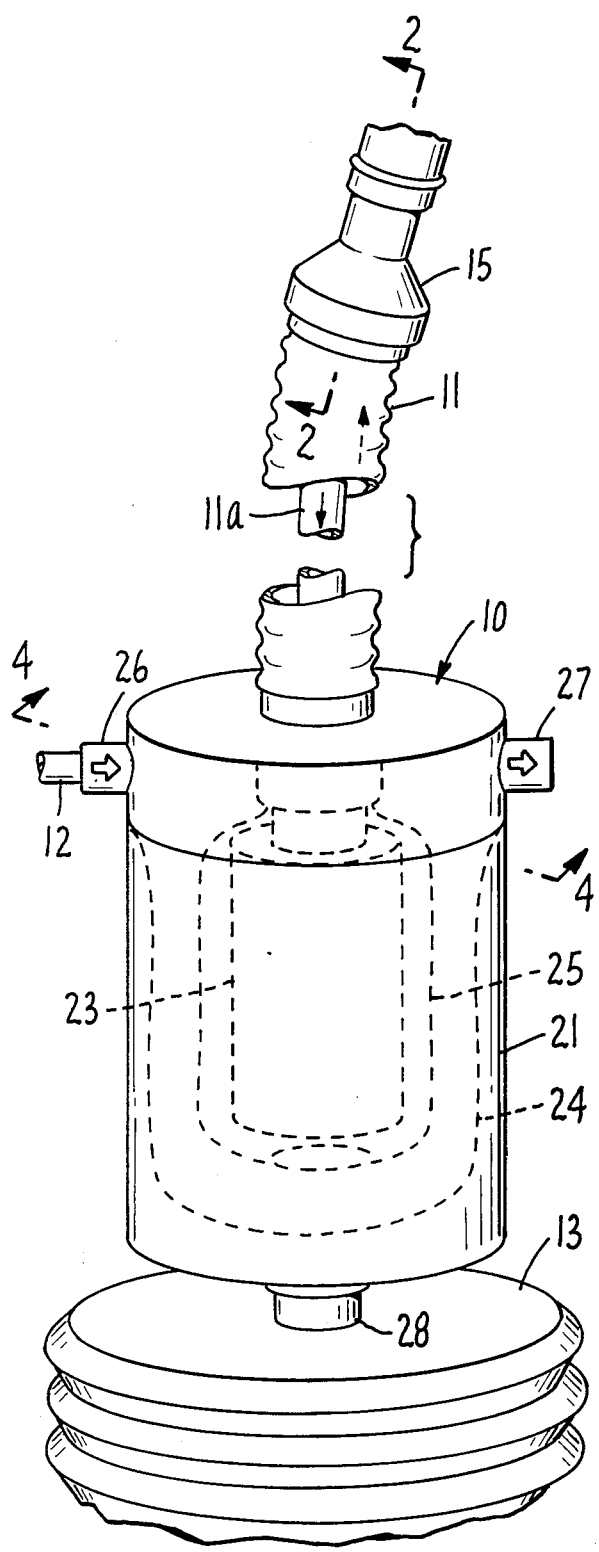
Figure 2:
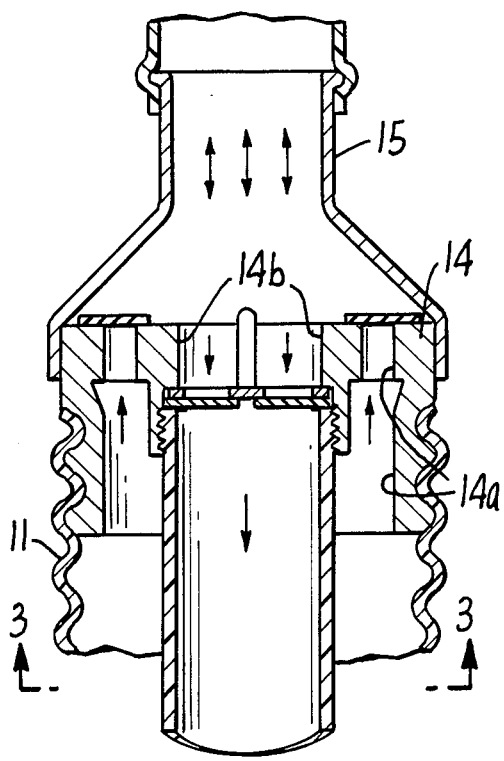
FIG. 2 is a center section through coaxial hose lines that connect between the canister and a patient's respiratory system.
Figure 3:
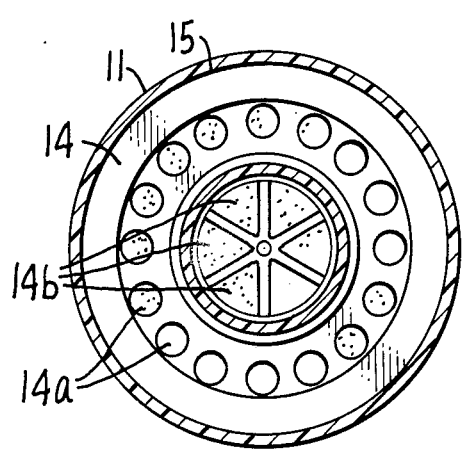
FIG. 3 is a section taken on line 3—3 of FIG. 2.

Referring to FIG. 1, a preferred embodiment of this invention comprises a disposable canister 10 that connects to a pair of coaxial lines 11 and 11a, a pressurized gas line 12, and a bellows 13. Coaxial lines 11 and 11a indirectly connect with the respiratory system of a patient through a directional flow valve 14 and a connical coupling 15. In general, oxygen and anesthesia introduced through gas line 12 pass through canister 10 into a passageway between lines 11 and 11a, then through passageways 14a of valve 14. Exhaled gases are returned through passageways 14b of valve 14. A valve disc 16 closes off passageways 14a upon exhalation of the patient, and a valve disc 17 closes off passageways 14b upon inhalation. The operation of such a valving structure is common to the art of rebreathing apparatus.

Figure 4:
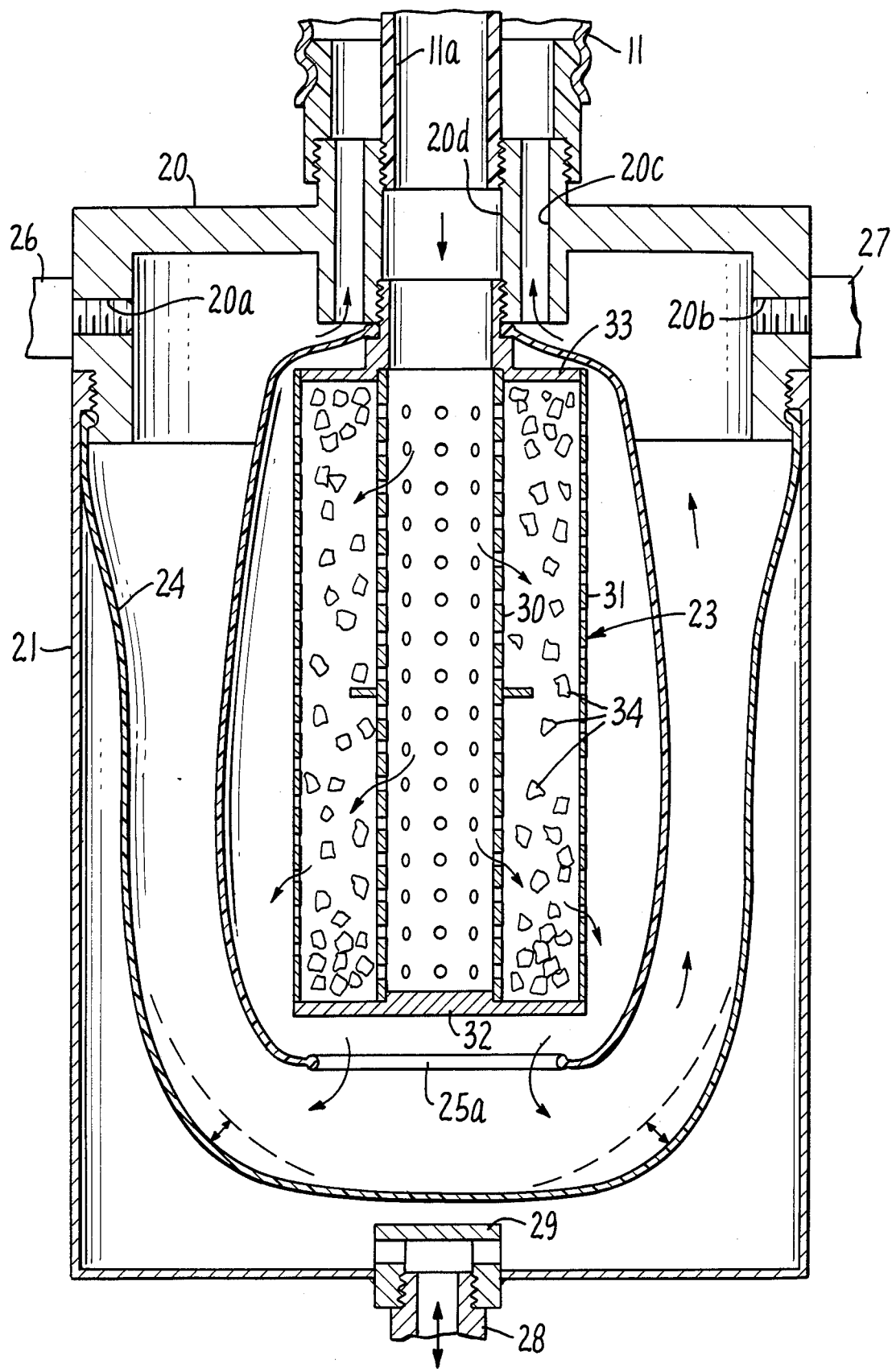
FIG. 4 is a center section of the disposable canister taken on the line 4—4 of FIG. 1.

Details of the present invention are more particularly shown in FIG. 4. Canister 10, essentially comprises a manifold plate 20, a rigid container 21, a $CO^2$ scrubber 23, a flexible liner 24, and a flexible shroud 25. Manifold plate 20 is formed with an intake port 20a that connects with a source of pressurized gas (oxygen and anesthesia) through a check valve 26. Plate 20 is also formed with an exhaust port 20b that discharges gas through a check valve 17. It will be apparent that check valve 26 prevents a return flow to the pressurized line 12 and check valve 27 allows only an exhaust flow of gases from the canister.

Manifold plate 20 is also formed with a pair of coaxial passages 20c and 20d. The innermost passage 20d connects with a cylindrical core passage 23a of filter 23, the outermost coaxial passages 20c being in open communication with intake port 20a and exhaust port 20b.

The lower end of container 21 is formed with an opening in the bottom that connects with bellows 13 through a stub connector 28. The opening is guarded by a deflector or a baffle 29. The bellows provides means for pressurizing the space between the rigid container and flexible liner 25 to assist in rebreathing; and it will be evident that liner 24 prevents contamination of container 21 as well as bellows 13 and, if desired, both may be reused with a new manifold and scrubber assembly.

In the preferred construction shown, manifold plate 20 and container 21 are substantially cylindrical and threadably connected. Liner 24 is formed as a bag-like receptacle having an upper lip that is engaged between surfaces of manifold 20 and container 21.

Scrubber 23 essentially comprises a perforated center core piece 30 and an outer perforated shell 31 connected at their lower ends by a plate 32 and at their upper ends by a tubular plate 33. Scrubber media 34, such as a soda-lime $CO_2$ absorbant, is contained within the cylindrical cavity defined by core piece 30, shell 31 and plates 32 and 33.

Flexible shroud 25 may be formed as a substantially cylindrical sleeve, the upper end thereof being sealingly engaged between surfaces of the manifold and scrubber the lower end extending below plate 32. Thus, flexible shroud 25 essentially encloses scrubber 23 but provides an opening 25a through which gases and moisture travel a tortuous passage, first passing downward through the opening, then upward between the liner and shroud, and finally through either exhaust port 20b or outer coaxial passage 20c of the manifold. This general filtering arrangement, and the purpose therefore, is described and shown in U.S. Pat. No. 4,502,876.

Although a preferred embodiment of the invention has been illustrated and described, various modifications and changes may be resorted to without departing from the spirit of the invention or the scope of the appended claims, and each of such modifications and changes is contemplated.

What is claimed is:

1. A canister for use with rebreathing apparatus and administering oxygen and anesthesia to a patient comprising:
   means for housing a scrubber including a manifold plate and a rigid container having an interior, said manifold plate having an intake port, an exhaust port and a pair of inner and outer coaxial passages;
   a flexible liner disposed within said rigid container and forming an imperforate barrier between the interior of said rigid container and the intake port, the exhaust port and the coaxial passages of said manifold plate;
   a scrubber having a cylindrical core passage connected to the inner one of said coaxial passages, and an exterior surface in fluid communication with said outer one of said coaxial passages and said intake and exhaust ports;
   and means for pressurizing the space between the interior of said rigid container and said flexible liner.

2. The filtering canister of claim 1 and further comprising a pair of check valves disposed in said intake and exhaust ports, respectfully.

3. The canister of claim 1 and further comprising a flexible shroud having an opening in the bottom thereof but which otherwise encloses said scrubber, forcing filtered gases and moisture to pass downwardly and travel a tortuous passage through the openings between the liner and shroud and then either through the exhaust port or through the outer coaxial passage of said manifold.

4. The canister of claims 1, 2, or 3 said rigid container having an opening therein, and bellows means connected to said opening for pressurizing the space between said rigid container and said flexible liner to assist in rebreathing.

5. The canister of claim 1, said manifold plate and container being substantially cylindrical and interconnected, said flexible liner being formed as a bag-like receptacle having an upper opening sealed between surfaces of said manifold and container.

6. The canister for claim 1 or 5, said manifold having a tubular portion that defines the inner one of said coaxial passages, said scrubber having a tubular plate at one end that connects to the tubular portion of said manifold.

7. The canister of claims 1 or 5, and further comprising a flexible shroud formed as a substantially cylindrical sleeve that surrounds said scrubber and having upper and lower ends, the upper end of the sleeve being sealed between surfaces of said manifold and filter, the lower end of the sleeve extending below the lower end of said scrubber.

* * * * *